(12) United States Patent
Lovi-Vilorey et al.

(10) Patent No.: US 10,925,993 B2
(45) Date of Patent: Feb. 23, 2021

(54) DIFFUSION DEVICE

(71) Applicant: Atelier Elio SA, Paris (FR)

(72) Inventors: Pierre Lovi-Vilorey, Paris (FR); Didier Gourand, Ivry sur Seine (FR); Eve Coutard, Paris (FR); Frederic Lambercy, Vallorbe (CH)

(73) Assignee: Atelier Elio SA, Paris (FR)

( * ) Notice: Subject to any disclaimer, the term of this patent is extended or adjusted under 35 U.S.C. 154(b) by 0 days.

(21) Appl. No.: 15/748,406

(22) PCT Filed: Jul. 29, 2016

(86) PCT No.: PCT/FR2016/051994
§ 371 (c)(1),
(2) Date: Jan. 29, 2018

(87) PCT Pub. No.: WO2017/017394
PCT Pub. Date: Feb. 2, 2017

(65) Prior Publication Data
US 2018/0214594 A1    Aug. 2, 2018

(30) Foreign Application Priority Data

Jul. 30, 2015    (FR) ...................................... 1557328

(51) Int. Cl.
*A61L 9/12*       (2006.01)
(52) U.S. Cl.
CPC ......... *A61L 9/122* (2013.01); *A61L 2209/133* (2013.01); *A61L 2209/134* (2013.01)

(58) Field of Classification Search
CPC ............... A61L 9/122; A61L 2209/134; A61L 2209/133
See application file for complete search history.

(56) References Cited

U.S. PATENT DOCUMENTS 4,629,604 A * 12/1986 Spector ............... A01M 1/2077
                                                      261/DIG. 88
5,622,543 A *  4/1997 Yang ....................... B03C 3/011
                                                      55/485
9,500,092 B2* 11/2016 Errick .................. B60H 1/3407
(Continued)

FOREIGN PATENT DOCUMENTS

| DE | 102010032122 A1 | 1/2012 |
|---|---|---|
| FR | 3020953 A1 | 11/2015 |
| GB | 2268798 A | 1/1994 |

OTHER PUBLICATIONS

International Search Report from corresponding International Patent Application No. PCT/FR2016/051994, dated Feb. 6, 2017.

*Primary Examiner* — Sean E Conley
*Assistant Examiner* — Brendan A Hensel
(74) *Attorney, Agent, or Firm* — Kusner & Jaffe

(57) ABSTRACT

A device for diffusing a volatile substance, comprising a housing defining internally an air circuit for the circulation of air between at least one air inlet and at least one air outlet, a ventilation means arranged in the circuit and able to circulate an air flow from the air inlet to the air outlet, and a receiving area arranged in the air circuit downstream of the ventilation means and intended to receive a substrate holding a volatile substance. The air circuit comprises at least one chamber arranged downstream of said receiving area and upstream of an air outlet of the housing.

22 Claims, 10 Drawing Sheets

(56) References Cited

U.S. PATENT DOCUMENTS

| | | |
|---|---|---|
| 2003/0186643 A1 | 10/2003 | Feuillard et al. |
| 2006/0285269 A1* | 12/2006 | Ohtsuka ................ F25D 17/042 |
| | | 361/225 |
| 2008/0093474 A1 | 4/2008 | Suissa et al. |
| 2010/0243754 A1 | 9/2010 | Harris |
| 2011/0139889 A1 | 6/2011 | Ohtsuka et al. |
| 2014/0051344 A1 | 2/2014 | Guggenheim et al. |
| 2015/0115060 A1* | 4/2015 | Klemm ................ A01M 1/2033 |
| | | 239/152 |
| 2017/0296689 A1* | 10/2017 | Peterson ................ A61L 9/122 |

* cited by examiner

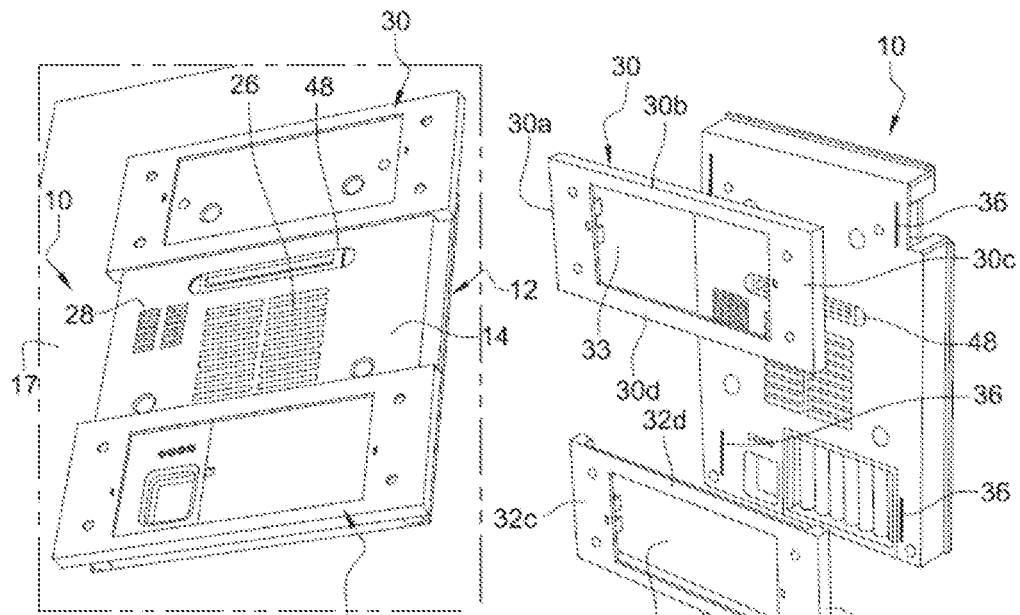
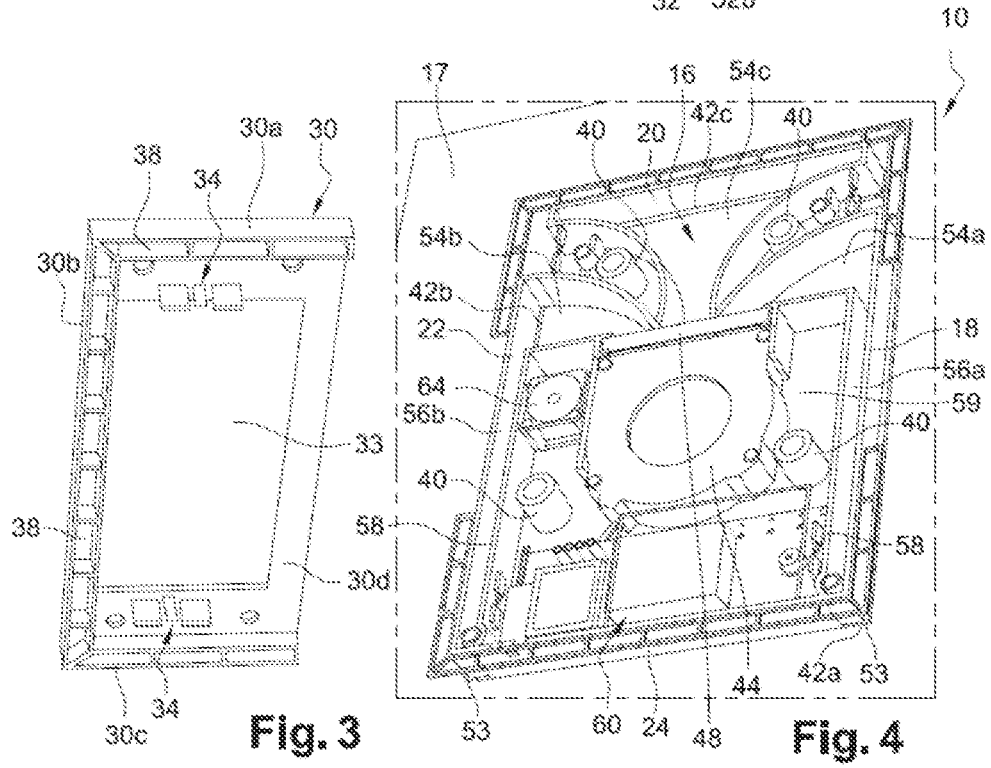

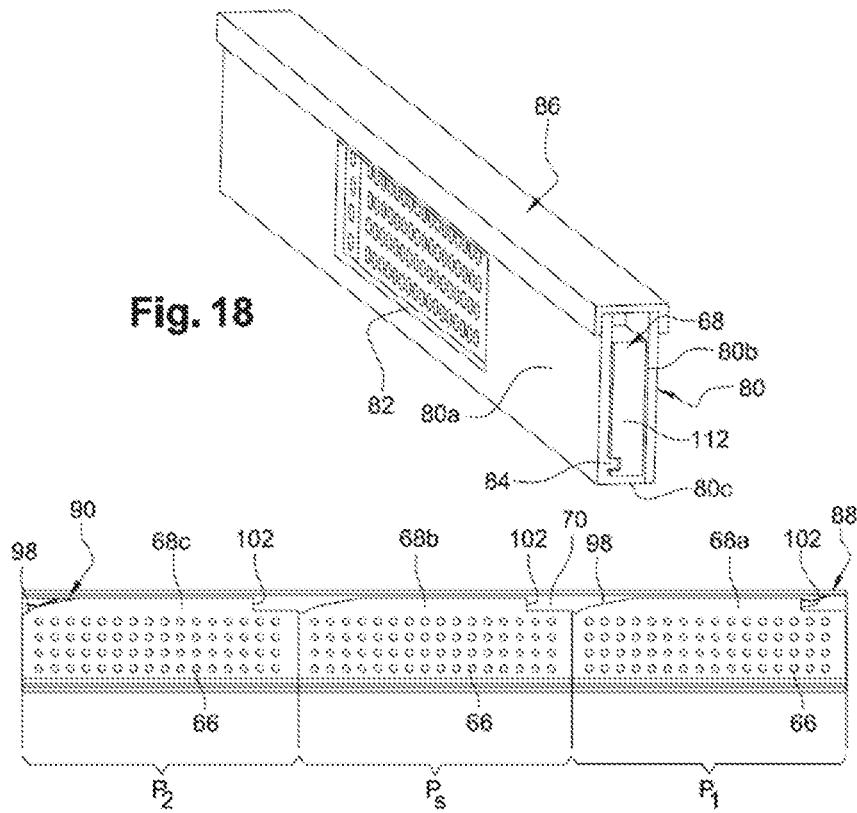
Fig. 18
Fig. 19
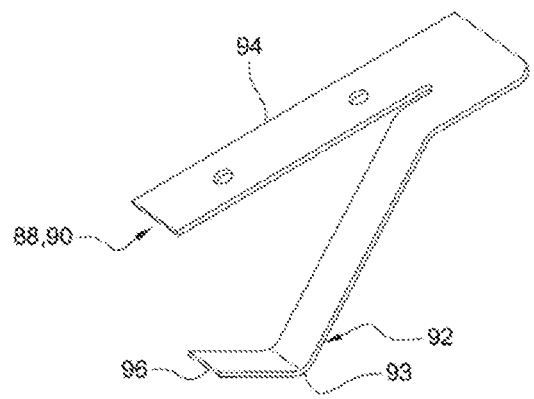
Fig. 20

DIFFUSION DEVICE

FIELD OF THE INVENTION

The present invention relates to a device for diffusing into the air a volatile compound, preferably fragrant, intended for example to be masked by a decorative object or a mirror for example.

BACKGROUND OF THE INVENTION

A diffusion device comprising a housing accommodating an air circulation circuit in which a ventilation means and bottles of bacterial and odour-diffusing products are arranged is known from the patent FR 1401085. The housing comprises lateral walls provided with air passage openings. In operation, the ventilation means allows a circulation of air containing particles coming from the bottles of bacterial and odour-diffusing products through the outlet orifices in the lateral walls, which makes it possible to spread said products in the surrounding atmosphere in which the diffusion device is installed.

Though this type of system is simple to implement, it is however clear that the air is not diffused uniformly through the various air outlet orifices, which does not make it possible to have uniform diffusion of the air over the required diffusion surface, the air pressure decreasing, the further away the orifices are from the ventilation means.

In addition, it also turns out that the diffusion of the fragrant volatile compound does not take place over a wide area in space, thus not affording good propagation of the fragrant volatile compound in a suitable manner.

SUMMARY OF THE INVENTION

The aim of the invention is in particular to afford a simple, effective and economical solution to the problems of the prior art described above.

To this end, it proposes a first device for diffusing a volatile substance, comprising:

a housing defining internally a circuit for the circulation of air between at least one air inlet and at least one air outlet, a ventilation means arranged in the air circuit of the housing and able to circulate an air flow from the air inlet to the air outlet, and a receiving area arranged in the air circuit downstream of the ventilation means and intended to receive a substrate holding a volatile substance, preferably fragrant, characterised in that the air circuit comprises at least one chamber arranged downstream of said receiving area and upstream of an air outlet of the housing.

Preferably, the device comprises three chambers that are fluidically independent of each other, each of the chambers being arranged downstream of said receiving area and communicating downstream with its own air outlet different from the other air outlets, first and second chambers communicating with air outlets projecting air in opposite directions, and a third chamber communicating with an air outlet that projects air in a direction perpendicular to the direction of projection of air discharged from the first and second chambers.

Integrating three diffusion chambers each connected to its own air outlet makes it possible better to diffuse the volatile substance in a wide area in space outside the housing. The air can thus be diffused uniformly in the external air, avoiding an unpleasant impression of an excessively high concentration at certain points in a room, as is the case with the appliances of the prior art.

According to another feature, the cross section of the chamber or chambers increases from upstream to downstream.

The cross sections of the chambers of the air circuit may have a cross section that increases on going downstream, which makes it possible, in operation, to achieve an accumulation of the volatile substance in the chamber. In addition, the fact that the chamber emerges directly in an air outlet of the housing makes it possible to achieve a direct diffusion of the air containing volatile product outside the housing and over a large diffusion surface area because of the increase in the cross section of the chamber in the downstream direction.

It may be desirable for the cross section of at least one or of each air outlet to be less than the downstream cross section of the chamber associated with the air outlet. In this way, it is possible to achieve an accumulation of the volatile substance in the chamber for a flow rate of the ventilation means at least equal to a threshold value, which makes it possible to ensure good diffusion of the perfume over the entire air outlet.

According to yet another feature, the housing may comprise a first bottom wall and a second bottom wall, which may be substantially parallel to one another and between which at least first, second and third lateral walls extend, one edge of each of the first, second and third lateral walls defining with an edge of one of the first and second bottom walls respectively an air outlet slot of the first, second and third chambers. The first lateral wall and the second lateral wall may be substantially parallel to one another and be arranged facing one another. The third lateral wall may be substantially perpendicular to the first and second lateral walls. The first and second bottom walls may be perpendicular to the first, second and third lateral walls.

The air outlets are thus formed by slots between the first, second and third lateral walls and one of the first and second bottom walls of the housing, which makes it possible to diffuse the air containing volatile particles coming from the substrate over the entire extent of the air outlet slots.

Preferentially, each air outlet extends all along one side of the housing so that the air can diffuse over an entire side of the housing and further improve diffusion, in operation, of the volatile substance.

The present description also relates to a second device comprising:

a housing comprising internally a circuit for the circulation of air between at least one air inlet and at least one air outlet, a ventilation means arranged in the air circuit and able to circulate an air flow from the air inlet to the air outlet, and a receiving area arranged in the air circuit downstream of the ventilation means and intended to receive a substrate holding a volatile substance, preferably fragrant, this device further comprising:

a path for movement of the substrate formed inside the housing and extending between a first opening and a second opening both formed in walls of the housing and accessible from the outside of the housing, and means for guiding the movement of the substrate along the movement path that intercepts the air circuit at the receiving area.

Thus the housing comprises a path for movement of the substrate inside the housing between first and second openings so that an operator can manually insert a substrate, from outside the housing, through the first opening for example, and recover it after use (several months for example) through the second opening for example.

It will be understood that the features of the second diffusing device may be integrated in the first diffusion device so as to form a third diffusion device, as will be clear by way of example in the detailed description.

The features indicated below may be integrated in at least one of the first, second or third devices.

According to another feature, the movement path may be sized so as to house at least three substrates arranged end to end in a first storage position, a service position in which the substrate is in the receiving area, and a second storage position.

In this configuration, when the movement path is sized so as to have a length equal to or similar to that of three substrates and houses three substrates, the insertion of the substrate in the first opening causes the following movements:

the substrate inserted through the first opening is positioned in the first storage position;

the substrate that is in the first storage position is moved into the service position;

the substrate that is in the service position is moved into the second position, and the substrate that is in the second storage position is ejected from the housing.

Preferentially, the first opening is formed in the first lateral wall and the second opening is formed in the second lateral wall.

In a particular configuration of the invention, the guidance means comprise a U-shaped rectilinear rail extending between the first opening and the second opening and internally delimiting the movement path of a substrate.

The guide rail may comprise a rectilinear guide member extending between the first opening and the second opening, this member being able to cooperate with a complementary guide member formed on each of the substrates.

More specifically, the guide member may comprise a rectilinear rib formed in one arm of the U-shaped rail.

The movement path may comprise, at the first opening, a resilient non-return member allowing the introduction of a substrate into the first opening and preventing removal thereof from the movement path through the first opening.

The movement path may comprise, at the second opening, a resilient restriction member configured so as to restrict the discharge of a substrate through the second opening.

In this way, introducing a substrate into the movement path is possible only in the first opening and removing a substrate is possible only in the second opening.

The rail may be covered by a rectilinear cover, preferably in a U shape, carrying at one end the resilient non-return member and at another end the resilient restriction member.

Equally, the resilient non-return member and the resilient restriction member may comprise an elastic blade, which may have the same shape.

One of the first and second bottom walls may comprise an opening emerging in the receiving area, a substrate holder being able to be conformed so as to be able to be forcibly inserted in the opening for positioning the substrate in the receiving area.

The receiving area designed to house the substrate holder itself carrying the substrate including the fragrant volatile compound is thus accessible from the outside, which makes it possible to perform a maintenance operation simply and quickly on the diffusion device when the substrate has to be replaced.

The housing may also comprise an internal chamber fluidically isolated from the air circuit and inside which means for controlling the fan and electrical supply means are housed, these means being thus isolated from the air circuit.

According to another feature, at least one support frame may be fixed to the first wall and comprise support means formed projecting on at least part of the contour of the housing and able to cooperate with means for attaching an object.

The invention also relates to an assembly comprising a device as described above and a substrate conformed so as to be able to be arranged in said receiving area.

Advantageously, the substrate has a substantially parallelepipedal form, for example rectangular, and comprises a plurality of holes emerging on two opposite faces of the substrate.

At least some of the orifices may have a cross section reducing from one end towards the other end.

Advantageously, the substrate is arranged in the receiving housing so that the cross section reduces from upstream to downstream.

According to another feature, the substrate may have a cross section with a roughly rectangular shape comprising at a first vertex an obliquely inclined ramp and at a second vertex a hollow.

The invention also relates to a substrate, such as a substrate for a device for diffusing a fragrant volatile substance, in which the substrate is solid, includes a volatile substance and comprises an upstream face and an opposite downstream face between which orifices extend for the circulation of air through the substrate, the substrate comprising a first end for insertion in a diffusion device and a second opposite end, the first end comprising a ramp intended to cooperate with a resilient non-return member and a second end comprising a hollow, a surface of which is intended to form a stop surface for the non-return member.

According to another feature of the invention, the substrate has a substantially parallelepipedal shape. Along a cutting plane interposed between the upstream and downstream faces and passing through the first and second ends, the substrate is in the form of a parallelogram, the ramp being situated at a first vertex arranged on the same side as the first end of the substrate and the hollow being situated at a second vertex situated on the same side as the second end of the substrate.

The form of the substrate may be substantially rectangular and/or the first vertex and the second vertex may be connected by the same edge extending between the first and second ends of the substrate.

The ramp may be substantially planar and obliquely inclined.

The invention will be understood better and other details, advantages and features of the invention will emerge from a reading of the following description given by way of non-limitative example, with reference to the accompanying drawings.

BRIEF DESCRIPTION OF THE DRAWINGS

FIG. 1 is a schematic perspective view from the outside of the diffusion device according to the invention;

FIG. 2 is a schematic perspective view of the device of FIG. 1 with an exploded view of the members intended to support a decorative element for example;

FIG. 3 is a schematic isolated perspective view of a support member of FIG. 2;

FIGS. 4 to 6 are schematic perspective views along different cutting planes of the diffusion device of FIG. 1;

FIGS. 18 and 19 are schematic views of the rail guiding the substrates according to the second embodiment;

FIG. 20 is a schematic perspective view of a resilient ember used for inserting the substrate;

DETAILED DESCRIPTION OF THE INVENTION

Figure 5:
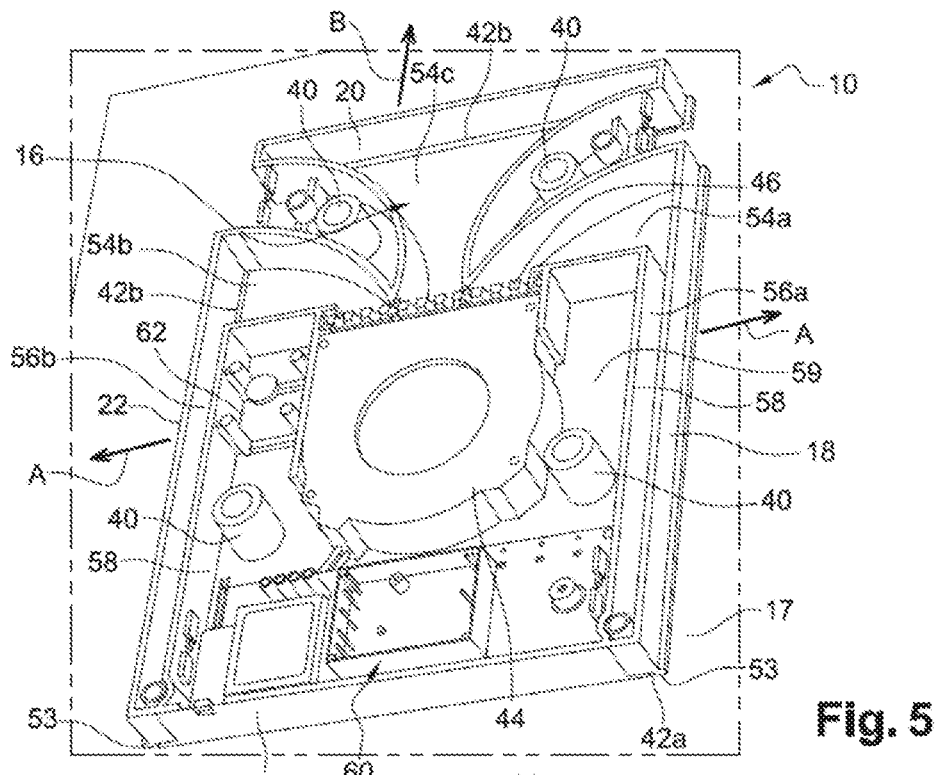

Reference is made simultaneously to FIGS. 1, 2, 4, 5, 6 and 10, which show a device 10 for diffusing a volatile substance according to the invention, comprising a housing 12, with an overall shape corresponding to a right-angled parallelepiped, which comprises a first bottom wall 14 and a second bottom wall 16. These first 14 and second 16 bottom walls are planar, arranged at a distance from one another and substantially parallel to one another. The second wall 16 is a wall intended to come into contact with a vertical support 17 such as an internal wall of a dwelling, while the first wall 14 is intended to come opposite a decorative object or a mirror for example. Lateral walls 18, 20, 22, 24 extend between the first bottom wall 14 and the second bottom wall 16 and define together the external periphery of the housing 12. The lateral walls 18, 20, 22, 24 are planar and substantially perpendicular to the first 14 and second 16 bottom walls. Thus the presence can be seen of a first lateral wall 18 and a second lateral wall 22 parallel to one another and facing one another as well as a third lateral wall 20 and a fourth lateral wall 24 parallel to one another and facing one another. The first 18 and second 24 lateral walls are perpendicular to the third 20 and fourth 24 lateral walls.

The first bottom wall 14 comprises two grilles 26, 28 with rectangular-shaped openings forming in one case an air inlet grille 26 for an air circuit and in the other case a grille 28 for the passage of audible sounds, as will emerge more clearly in the remainder of the description. The first grille 26 is arranged substantially centrally on the first wall 14.

As shown in FIGS. 1, 2, and 3, the diffusion device 10 comprises support means intended to support a decorative object or a mirror. To this end, the support means comprise a first support frame 30 mounted at a first end of the housing 12 and applied to the first wall 14, and a second support frame 32 mounted at a second end of the housing 12 opposite to the first end and applied to the first wall 14. Each first frame 30 and second frame 32 is formed in a single piece and comprises first 30a, 32a, second 30b, 32b, third 30c, 32c and fourth 30d, 32d successive uprights defining together a rectangle internally delimiting a central opening 33. The first upright 30a, 32a and the third upright 30c, 32c of each frame 30, 32 carry resilient members 34 for snapping in slots 36 in the first wall 14. The first 30a, 32a, second 30b, 32b and third 30c, 32c uprights comprise a succession of rectangular recesses 38 intended to receive means for attaching a decorative object or a mirror. It will be noted that each frame 30, 32 is sized so that the recesses 38 are arranged projecting on the periphery of the housing 12 in order to allow an engagement of means for attaching a decorative object in the recesses.

The first 14 and second 16 bottom walls are connected by tubular passages 40 intended to receive screws for fixing the diffusion device on a support of a dwelling such as a wall for example. As can be seen in FIG. 1, two tubular passages 40 pass through the opening 33 of the first frame 30 while the other two tubular passages 40 pass through the first bottom wall 14 and the second bottom wall 16 so as to emerge on the first bottom wall 14 between the first 30 and second 32 support frames. The arrangement of the tubular passages 40 is determined according to the space available in the housing 12 for mounting elements necessary for the functioning of the diffusion device 10, as will emerge more clearly in the remainder of the description.

The housing 12 comprises an air circuit, the air inlet of which is formed by the grille 26 of the first bottom wall 14 of the housing 12 as indicated previously and a plurality of outlets 42a, 42b, 42c, a first air outlet 42a, a second air outlet 42b and a third air outlet 42c. The air circuit comprises a ventilation means 44 aspirating air from the outside through the grille 26 and ejecting air through a substrate 46 or cartridge arranged downstream of the ventilation means 44. The substrate 46 is carried by a substrate holder 48 that is inserted in a receiving area 50 arranged immediately downstream of the ventilation means. This receiving area 50 is accessible from the outside of the housing 12, by means of an opening 52 in the first bottom wall 14 with a shape complementary to that of the substrate holder 48 and emerging in the receiving area 50. The opening 52 in the first bottom wall 14 and the substrate holder 48 are sized with respect to one another so that the substrate holder 48 is forcibly inserted in the opening 52 in the first bottom wall 14 in order to be housed in the receiving area 50 of the air circuit and to be able to be held therein. The substrate holder 48 is formed by a rectangular frame made from rigid material in which the substrate 46 can be introduced before the assembly consisting of substrate holder 48 and substrate 46 is positioned in the air circuit (FIGS. 1, 6, 7 and 9). When the housing 12 is attached to a wall for example, the second bottom wall 16 is arranged facing the wall and the first bottom wall 14 is arranged opposite, which allows access to the opening 52 in order to be able to carry out maintenance of the device, thus making it possible to remove the substrate holder 48 in order to withdraw the used substrate and to insert a new substrate 46 therein.

The air circuit comprises three chambers, a first diffusion chamber 54a, a second diffusion chamber 54b and a third diffusion chamber 54c arranged downstream of the receiving area 50 of the substrate 46, the first chamber 54a communicating with the first air outlet 42a, the second chamber 54b communicating with the second air outlet 42b and the third chamber 54c communicating with the third air outlet 42c of the housing 12. The first air outlet 42a is formed by a rectilinear slot delimited between one edge of the first lateral wall 18 of the housing 12 and a peripheral edge of the second bottom wall 16. The second air outlet 42b is formed by a rectilinear slot delimited between one edge of the second lateral wall 22 of the housing 12 and a peripheral edge of the second bottom wall 16. The third air outlet 42c is formed by a rectilinear slot delimited between one edge of the third lateral wall 20 of the housing 12 and a peripheral edge of the second bottom wall 16. Each slot 42a, 42b, 42c thus extends all along the edge of a lateral wall 18, 20, 22 and the peripheral edge of the second wall 16 (FIG. 8).

Figure 8:
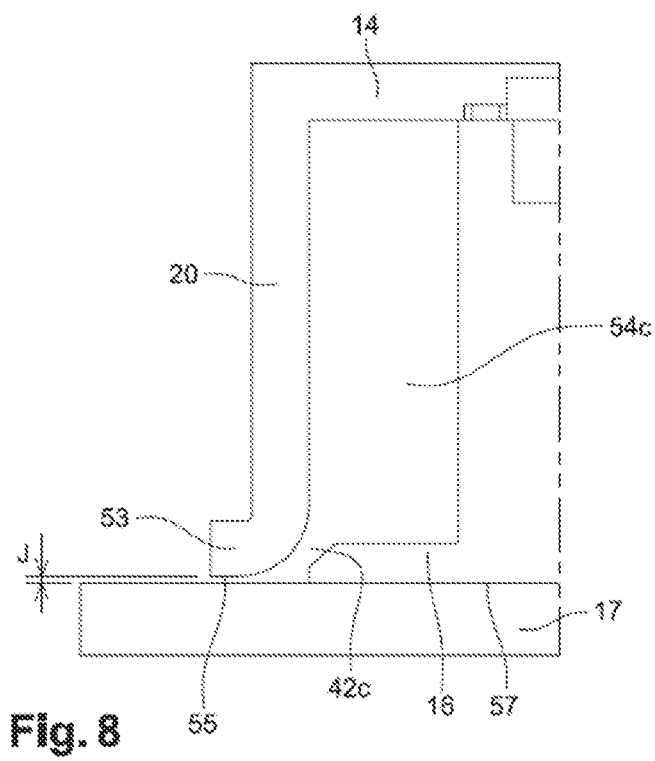
FIG. 8 is a schematic view in cross section of an air outlet of the diffusion device according to the invention.

As can be seen more particularly in FIG. 8, the third lateral wall 20 carries a rim 53 extending towards the outside of the housing 12 in a direction perpendicular to the third lateral wall 20. This rim 53 is conformed so that its face 55 oriented facing the wall 17 is arranged at a distance therefrom. More particularly, in a direction perpendicular to the second bottom wall 16, the face 55 is spaced by a clearance J from the external face 57 of the second bottom wall 16, which allows a flow of air towards the outside on the periphery of the housing 12. This clearance J is here less than the width of the second slot 42b. The first 18 and second 22 lateral walls may also comprise a rim identical to the rim 53 of the lateral wall and defining a clearance J with the external face 57 of the second bottom wall 16, as described above.

As shown, each of the first 54a, second 54b and third 54c chambers has a shape that splays from its upstream end to its downstream end. Thus the cross section of each chamber 54a, 54b, 54c increases from its upstream end to its downstream end, which communicates with an air outlet 42a, 42b, 42c.

More particularly, the first 54a and second 54b chambers communicate with air slots 42a, 42c projecting air in opposite directions along a first axis (arrows A). The third chamber 54c communicates with the slot 42c, which projects air in a second direction (arrow B) substantially perpendicular to the projection direction of the slots 42a, 42b, for example in a direction oriented upwards when the housing is positioned suitably. According to the invention, each chamber 54a, 54b, 54c is associated with an air outlet slot 42a, 42b, 42c independent of the other chambers 54a, 54b, 54c and air outlet slots 42a, 42b, 42c. It will be noted that the third chamber 54c is separated from the first chamber 54a and from the second chamber 54c by two tubular passages 40, 40.

Figure 6:
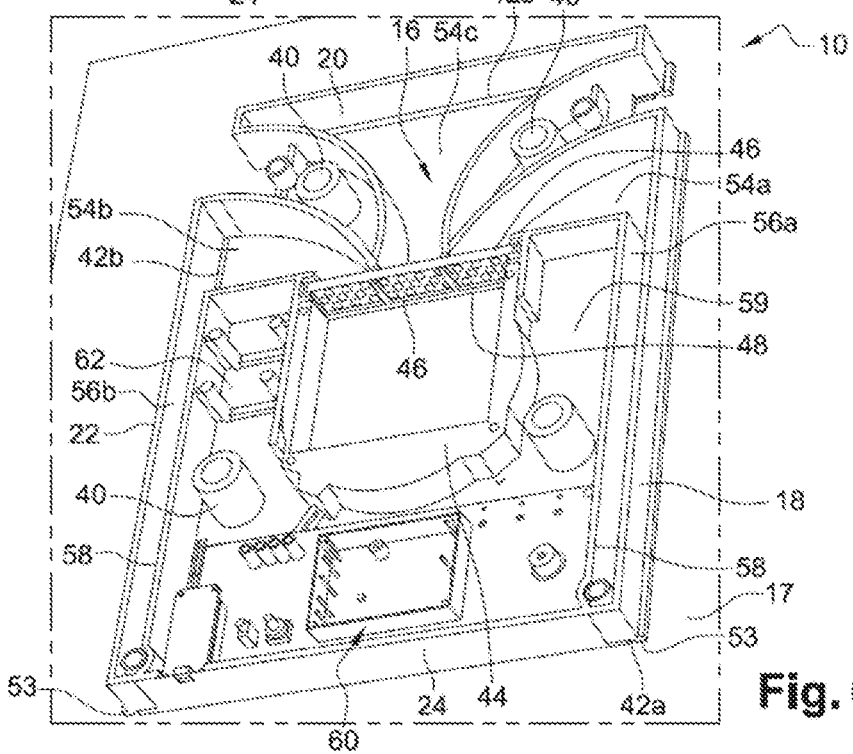

As can be seen in FIGS. 5 and 6 more particularly, the downstream portions of the first 54a and second 54b chambers comprise a downstream channel 56a, 56b intended to achieve a distribution of the flow all along the air outlet slot 42a, 42b. The channel 56a is delimited by the first lateral wall 18 and a facing partition 58 delimiting a part of an internal chamber 59. The channel 56b is delimited by the second lateral wall 22 and a facing partition 58 delimiting a part of the internal chamber 59. It will be noted that, thus configured, the first chamber 54a and its channel 56a are symmetrical with the second chamber 54b and its channel 56b with respect to a mid-plane of the third chamber 54c and perpendicular to the second bottom wall 16. More generally, the air circuit is symmetrical with respect to the aforementioned plane.

The internal chamber 59 is delimited by facing partitions 58, the fourth lateral wall 24 and the external envelope or casing of the ventilation means 44. This chamber is fluidically isolated from the air circuit and houses means for controlling the flow rate of the fan and electrical supply means 60. The internal chamber 59 may also comprise an enclosure 62 for a loudspeaker 64 connected to means for processing a digital signal issuing from an audio file coming from a USB key for example, which may be connected to a connector accessible from the outside of the housing (not shown).

Figures 10, 11:
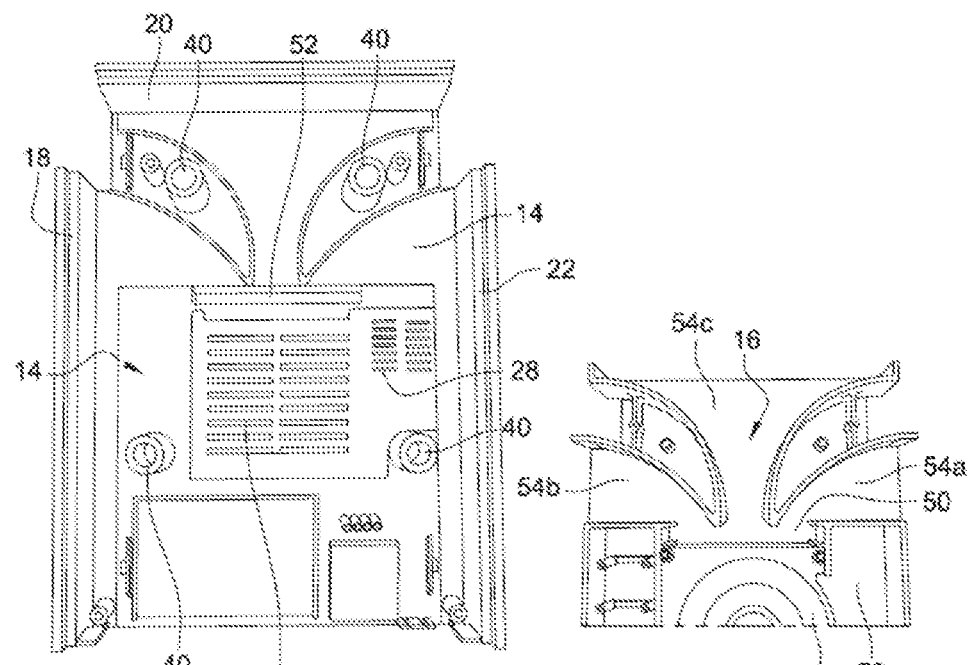
FIGS. 10 and 11 are schematic views of one possible practical embodiment of the invention.

In the configuration shown in FIGS. 10 and 11, the first 18, second 22 and third 20 lateral walls, defining with the second bottom wall 16 said first 42a, second 42b and third 42c air outlet slots, are secured to the first bottom wall 14, while the fourth lateral wall 24 is secured to the second bottom wall 16 (FIGS. 10 and 11). The tubular passages 40 are also secured to the first bottom wall 14.

Figure 7:
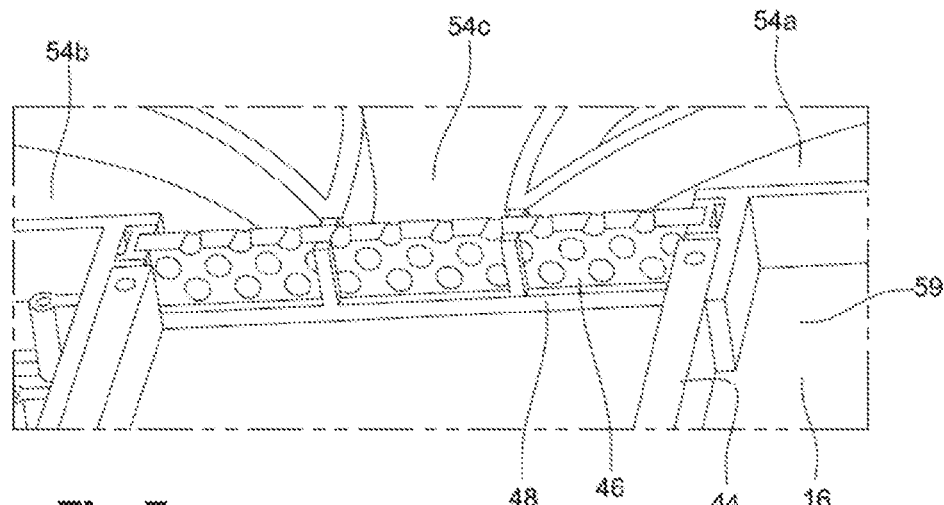
FIG. 7 is a schematic perspective view to a larger scale of the area delimited in broken lines in FIG. 6.
Figure 12:
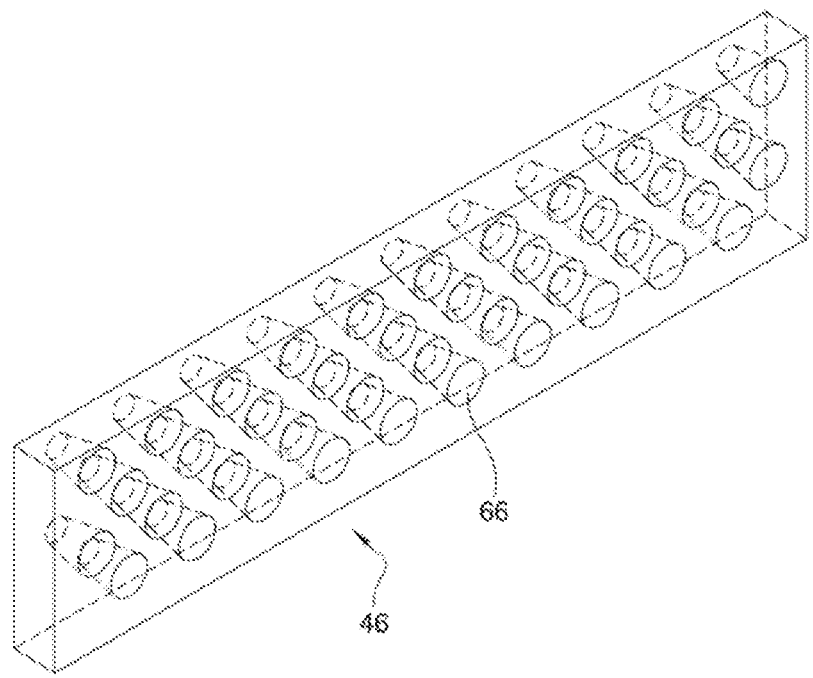
FIGS. 12 and 13 are schematic views of the orifices in a substrate holding a volatile substance.
Figure 13:
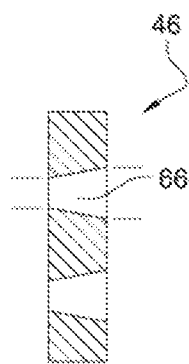

As can be seen more particularly in FIGS. 7, 12 and 13, the substrate 46, incorporating a volatile substance, has the appearance of a plate in the form of a right-angled parallelepiped or straight tile and has holes 66 with a frustoconical shape passing right through between its two largest faces. When the substrate 46 is mounted in the substrate holder 48 and the latter is arranged in the receiving area 50 of the air circuit, the holes 66 are oriented so that the cross section of each of them decreases in the upstream/downstream direction.

Figure 14:
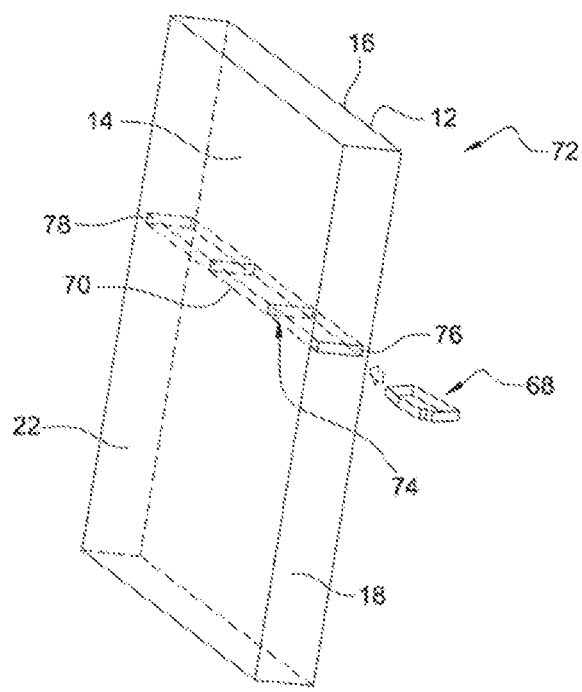
FIG. 14 is a schematic perspective view of a second embodiment of the device according to the invention.
Figure 15:
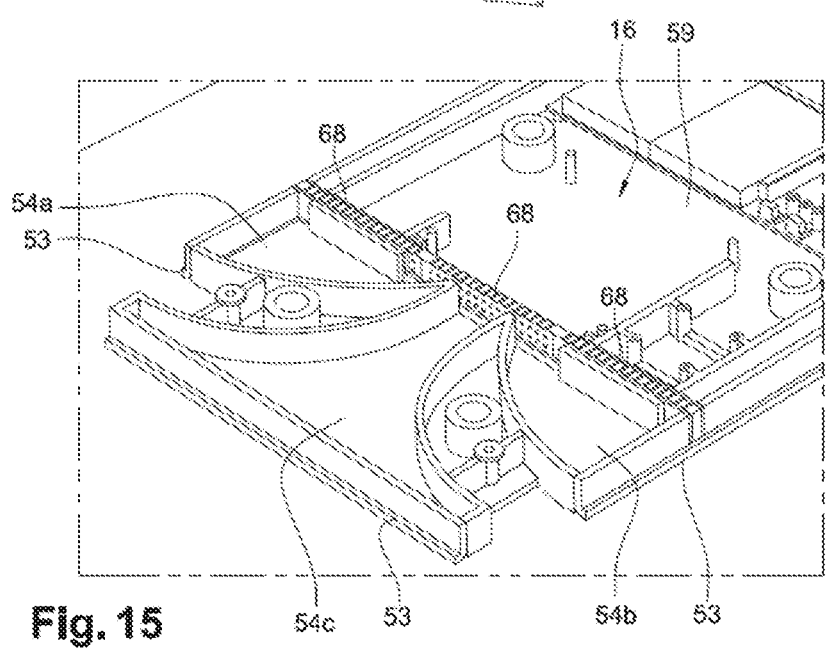
FIGS. 15 to 17 are schematic perspective views of the second embodiment of the device.
Figure 16:
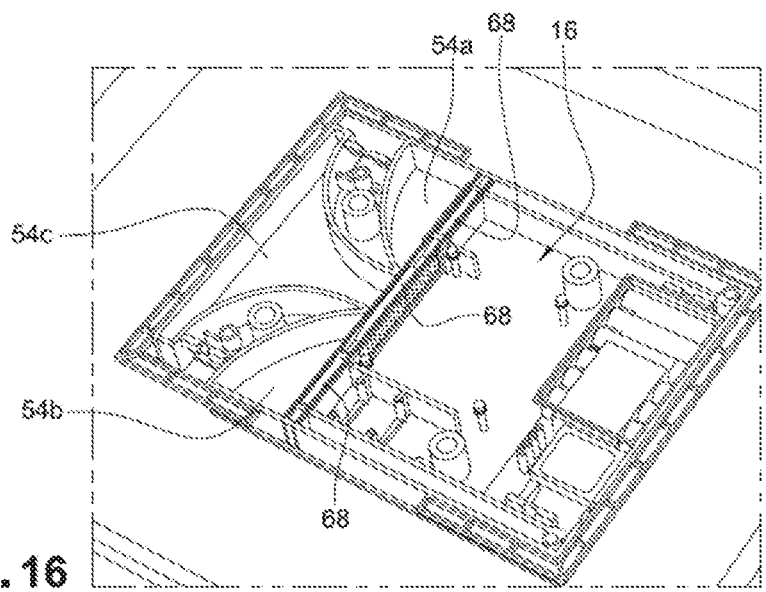
Figure 17:
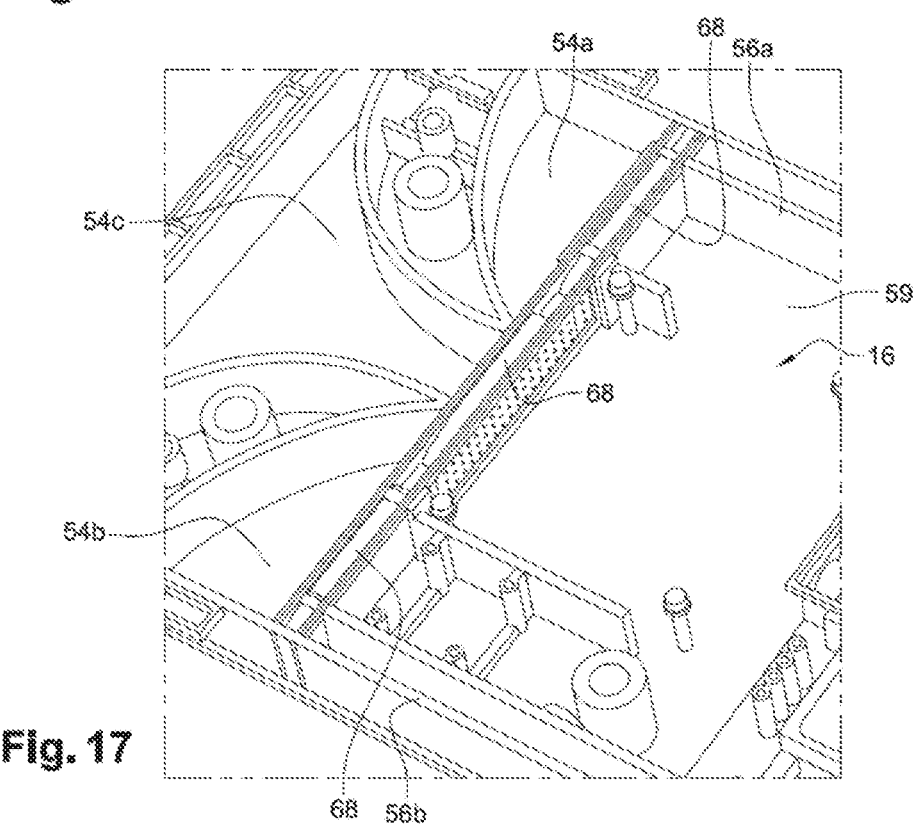
Figure 21:
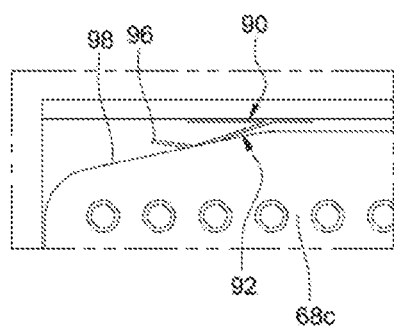
FIGS. 21 and 22 are schematic side views of opposite ends of the guide rail of FIG. 19.
Figure 22:
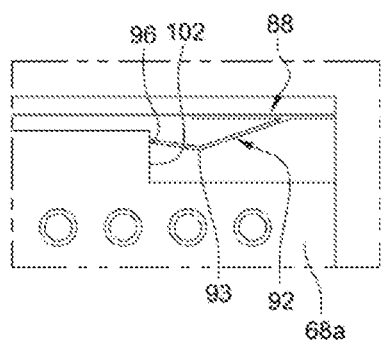

FIG. 14 and subsequent figures show a variant of integration of the substrate 68 or cartridge in the receiving area 70 of the device 72, the other features being identical to what was described previously. Thus, in this variant, the first bottom wall 14 does not comprise an opening emerging in the receiving area 70 but comprises a movement path 74 integrating the receiving area 70 and which is formed inside the housing 12 and extends between a first opening 76 formed on the first lateral wall 18 and a second opening 78 formed in the second lateral wall 22 (FIG. 14). This movement path 74 is substantially rectilinear and is perpendicular to the first 18 and second 22 lateral walls. As shown in FIGS. 15 to 17, the movement path 74 intercepts the air circuit at the receiving area 70 so that a substrate 68 introduced in the first opening 76, brought into the receiving area 70, can have the air of the air circuit pass through it.

The movement path 74 is sized so as to be able to house a plurality of substrates 68, in the example shown three substrates 68, arranged end to end. In this case, a first substrate 68a is arranged in a first storage position $P_1$ in which the first substrate 68a is not in the air circuit, a second substrate 68b is arranged in a service position $P_s$ in which the substrate is in the receiving area 70, and a third substrate 68c is arranged in a second storage position $P_2$ in which the substrate 68c is not in the air circuit. Thus the storage path comprises three successive positions, a first storage position $P_1$, a service position $P_s$ and a second storage position $P_2$ (FIG. 1)). It will easily be understood that a substrate 68 inserted in the first opening 76 of the movement path 74, the one already comprising three substrates 68a, 68b, 68c, causes the following movements:

the substrate 68 inserted through the first opening 76 is positioned in the first storage position $P_1$:

the substrate 68a that is in the first storage position $P_1$ is moved into the service position $P_s$;

the substrate 68b that is in the service position $P_s$ is moved into the second position $P_2$; and the substrate 68c that is in the second storage position $P_2$ is ejected from the housing 12.

As will emerge subsequently, the first storage position $P_1$ corresponds to a storage position of a substrate 68a or cartridge in the new state and the second storage position $P_2$ corresponds to a storage position of a substrate 68c in the used state, that is to say that has passed through the service position $P_2$.

Figure 23:
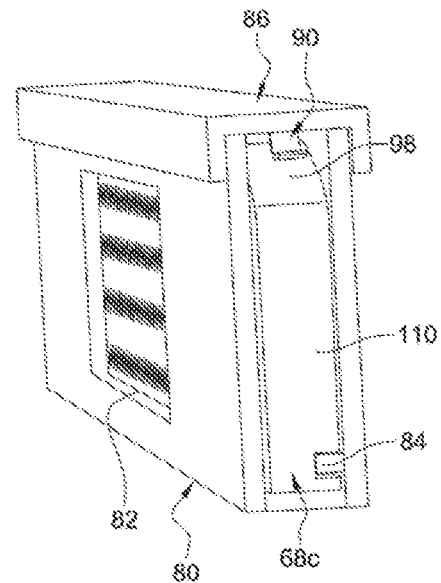
FIG. 23 is a schematic perspective view of the end of the rail shown in FIG. 21.
Figure 24:
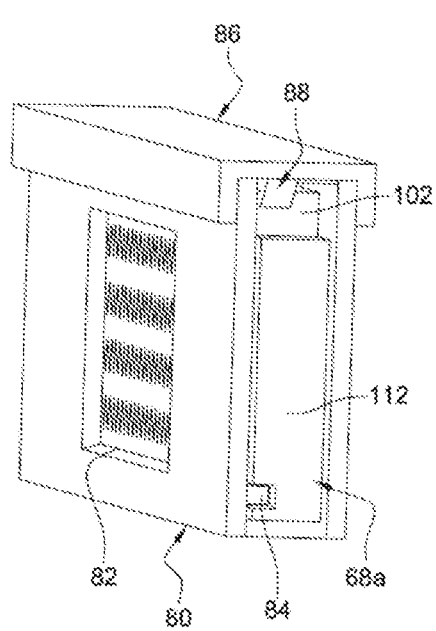
FIG. 24 is a schematic perspective view of the end of the rail shown in FIG. 22.

The device comprises means for guiding the movement of the substrate 68 along the movement path 74 (FIGS. 18, 23 and 24). These guide means comprise a rectilinear rail 80 extending between the first opening 76 and the second opening 78 and is housed inside the housing 12 between the first bottom wall 14 and die second bottom wall 16. This rail 80 delimits the movement path 74 of the substrates 68 internally. It is here sized so as to be able to completely house the substrates 68. The rail 80 has a U shape comprising a first arm 80a and a second arm 80b substantially parallel to one another and connected together by a junction wall 80c. The first arm 80a comprises an aperture 82 arranged facing an aperture 82 in the second arm 80b, the apertures 82 being positioned on the rail 80 so that the air circuit circulates through these apertures 82. The position of these apertures 82 thus corresponds to the service position $P_s$ of a substrate 68.

Figure 25:
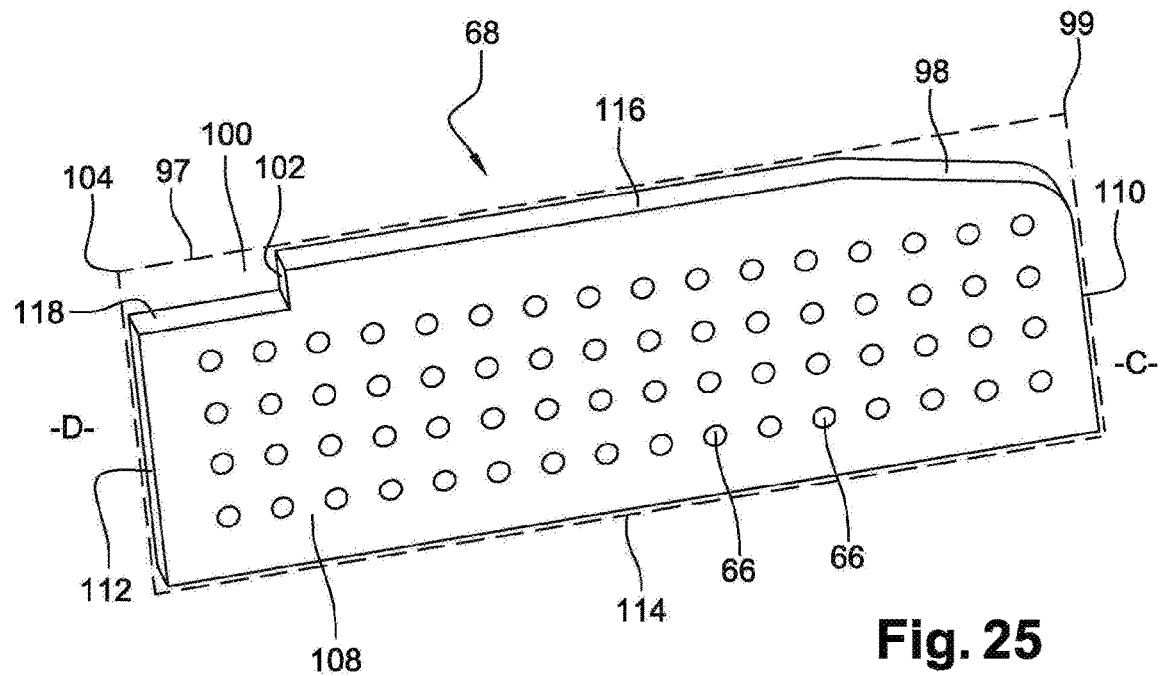
FIGS. 25 and 26 are schematic views of a substrate according to a valiant embodiment.
Figure 26:
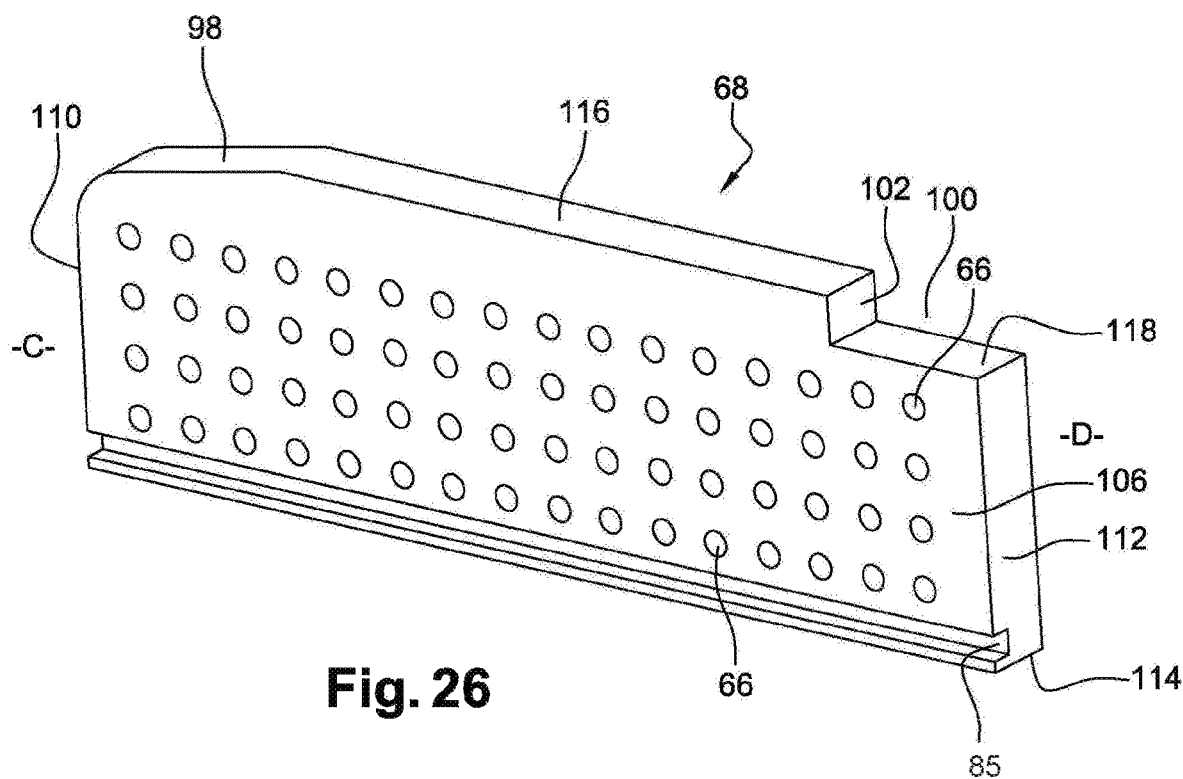

The first arm 80a comprises a guide member 84 formed by a rectilinear rib extending parallel to the junction wall 80c. This rib 84 cooperates with a groove 85 formed on the upstream face of each of the substrates 68 (FIGS. 25 and 26). The groove could be formed on the downstream face of the substrate 68 in order in this case to cooperate with a rib on the second arm 80b of the rail 80.

The rail 80 is covered by a rectilinear cover 86 having the form of a U-shaped profile. This cover 86 limits the separation of the arms 80a, 80b of the U-shaped rail 80. It carries two resilient members, one 88 arranged in the movement path 74 at the first opening 76 and providing a non-return function and another one 90 arranged in the movement path 74 at the second opening 78 and providing a restriction function (FIGS. 19 and 21 to 24).

The non-return resilient member 88 and the restriction resilient member 90 each comprise a spring blade 92 or resilient blade (FIG. 20) connected to a base 94 fixed by bolting to the cover 86. The resilient blade 96 has a V shape comprising a vertex or elbow 96. As shown in FIG. 19, the non-return resilient blade is arranged so that its free end 96 is directed towards the second opening 78 and the restriction resilient blade 92 is also arranged so that its free end 96 is oriented towards the second opening 78.

Each substrate 68 has a right-angled parallelepipedal form and has a cross section with a roughly rectangular shape shown in broken contours 97 (FIG. 26) along the cutting plane interposed between an upstream face 106 and the downstream face 108 and passing through a first end C of insertion of the substrate in the device and a second opposite end D (FIGS. 25 and 26). It comprises an obliquely inclined planar ramp 98 situated at a first vertex 99 of the rectangular contour 97 arranged on the same side as the first end C of the substrate 68, and a hollow 100 comprising a shoulder 102 formed at a second vertex 104 adjacent to the first vertex and situated on the same side as the second end D of the substrate 68. As shown, the first vertex 99 and the second vertex 104 are connected by the same edge extending between the first C and second D ends of the substrate 68.

The upstream 106 and downstream 108 faces of the substrate 68, with respect to the direction of circulation of the air flow, facing each other, have air-circulation orifices 66 passing through them, these orifices 66 being able to be frustoconical and with a cross section increasing towards the downstream end as indicated previously (FIGS. 25 and 26). These two faces 106, 108, parallel to one another, are connected to one another by junction faces. A first 110 and a second 112 junction face are parallel to one another and are arranged facing one another. The first junction face 110 and the second junction face 112 are connected by a third junction face 114. Finally, the substrate 68 comprises a fourth junction face 116 substantially parallel to the third junction face 114. This fourth junction face 116 is connected to the first junction face 110 by an inclined face or ramp 98 and is connected to the second junction face 112 by two successive faces 102, 118 of a hollow 100, one of the faces 102 of which forms a shoulder.

The device 72 according to the invention is used as follows. An operator introduces a substrate 68 into the movement path, arranging the first junction face 110 of the substrate 68 opposite the first opening 76. The substrate 68 is pushed inside the movement path 74, the non-return resilient blade comes into abutment on the ramp 98, or more precisely the angled portion or vertex of the V. Said angled portion next comes into abutment on the fourth junction phase 116 and then relaxes in the hollow 100, the free end 96 of the non-return resilient blade 88 coming to be positioned facing the stop surface formed by the shoulder 102, which provides locking of the substrate 68 in the first storage position $P_1$. It will be understood that introducing a substrate 68 into the first opening 76 simultaneously causes the discharge of a substrate 68 from the second opening 78, this discharge being restricted by the resilient abutment of the angled portion or vertex of the restriction blade 90 on the ramp 98, which limits the speed of ejection of the substrate 68 in the second storage position $P_2$ from the second opening 78.

Figure 9:
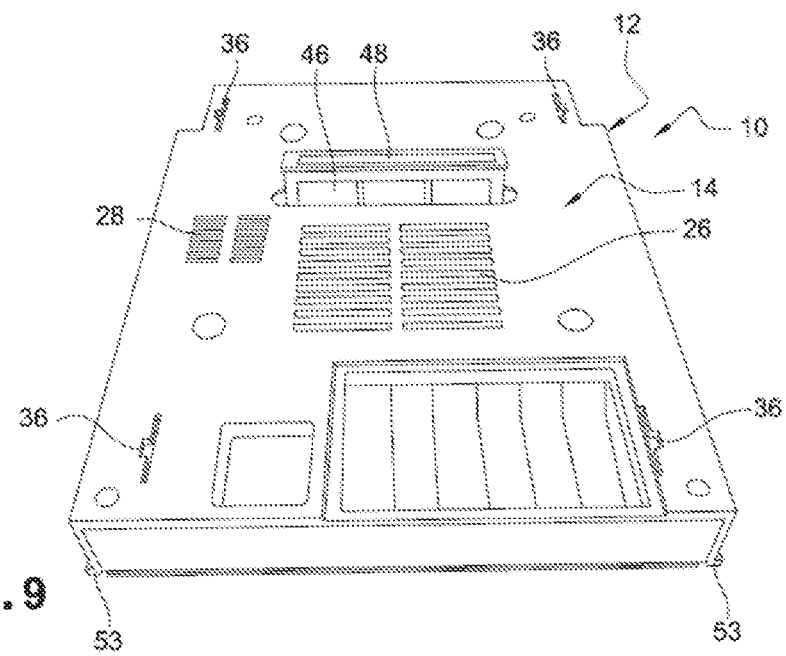
FIG. 9 is a schematic view of the diffusion device according to the invention, the substrate holding a volatile substance being in a partially emerged position.

It should be noted that the substrate 68 described with reference to FIGS. 25 and 26 is entirely suitable for being used with a substrate holder 48 as described with reference to FIG. 9.

In the present description, the term substrate 68 refers to a cartridge that could have any form so that the invention is not limited solely to the forms of cartridge described. This is because the substrate could have, along a cutting plane passing between an upstream face and a downstream face and through the first end and the second end, a circular or polygonal shape or the shape of a parallelogram, the upstream and downstream faces of the substrate being able to be planar and parallel to one another or inclined with respect to one another. These upstream and downstream faces could also not be planar and have more complex curved forms.

Likewise, the ramp could have in cross section a rectilinear or concave or convex form depending on the resistance that it is wished for the operator to exert on the non-return resilient member. The ramp may have, along a plane perpendicular to the aforementioned cross-section plane, a rectilinear shape or be concave or convex.

Having described the invention, the following is claimed:
1. A device for diffusing a volatile substance, comprising:
   a housing defining internally an air circuit for the circulation of air between at least one air inlet and at least one air outlet;
   a ventilator arranged in the air circuit of the housing and able to circulate an air flow from the air inlet to the air outlet; and
   a receiving area arranged in the air circuit downstream of the ventilator and intended to receive a substrate holding a volatile substance, wherein the air circuit comprises:
   at least three chambers that are fluidically independent of each other, each of the chambers being arranged downstream of said receiving area and communicating downstream with its own air outlet different from the other air outlets, said at least three chambers including first and second chambers communicating with air outlets projecting air in opposite directions, and a third chamber communicating with an air outlet that projects air in a direction perpendicular to the direction of projection of air discharged from the first and second chambers, wherein the housing comprises a first bottom wall and a second bottom wall, between which at least first, second and third lateral walls extend, wherein each of the air outlets of the first, second and third chambers is formed by a rectilinear slot defined between, and extending longitudinally parallel to, one edge of each of the first, second and third lateral walls and a peripheral edge of one of the first and second bottom walls respectively, wherein said one edge of each of the first, second and third lateral walls is parallel to the peripheral edge of one of the first and second bottom walls respectively.

2. The device according to claim 1, wherein the cross section of the chambers increases from upstream to downstream.

3. The device according to claim 1, wherein the device further comprises:
a movement path of the substrate formed inside the housing and extending between a first opening and a second opening both formed in walls of the housing and accessible from the outside of the housing; and
a guide configured to guide movement of the substrate along the movement path that intercepts the air circuit at the receiving area.

4. The device according to claim 3, wherein the movement path is sized so as to house at least three substrates arranged end to end in respectively a first storage position ($P_1$), a service position ($P_s$) in which the substrate is in the receiving area, and a second storage position ($P_2$).

5. The device according to claim 3, wherein the first opening is formed in the first lateral wall of the housing and the second opening is formed in the second lateral wall of the housing.

6. The device according to claim 3, wherein the guide comprise a U-shaped rectilinear rail extending between the first opening and the second opening and internally delimiting the movement path of the substrate.

7. The device according to claim 6, wherein the guide comprises a rectilinear guide member extending between the first opening and the second opening and able to cooperate with a complementary guide member formed on each of the substrates.

8. The device according to claim 7, wherein the guide member comprises a rectilinear rib formed in an arm of the U-shaped rectilinear rail.

9. The device according to claim 3, wherein the movement path comprises, at the first opening, a non-return resilient member allowing the introduction of a substrate in the first opening and preventing removal thereof from the movement path through the first opening.

10. The device according to claim 3, wherein the movement path comprises, at the second opening, a restriction resilient member configured so as to restrict the discharge of the substrate through the second opening.

11. The device according to claim 9, wherein the guide comprises a U-shaped rectilinear rail covered by a rectilinear cover, having a U shape, carrying at one end the non-return resilient member and at another end a restriction resilient member configured so as to restrict the discharge of the substrate through the second opening.

12. The device according to claim 9, wherein the non-return resilient member and a restriction resilient member configured to restrict the discharge of the substrate through the second opening each comprise a resilient blade.

13. An assembly comprising a device according to claim 1 and a substrate conformed so as to be able to be arranged in said receiving area.

14. The assembly according to claim 13, wherein the substrate has a parallelepipedal shape and comprises a plurality of holes emerging on two opposite faces of the substrate.

15. The assembly according to claim 13, wherein the substrate has a cross section that is substantially rectangular in shape, comprising at a first vertex an obliquely inclined ramp and at a second vertex a hollow.

16. The assembly according to claim 13, wherein
the substrate is solid,
includes a volatile substance, and
comprises an upstream face and an opposite downstream face between which orifices extend for the circulation of air through the substrate,
wherein the substrate comprises a first end (C) for insertion in a diffusion device, the substrate comprising a second opposite end (D), the first end (C) comprising a ramp intended to cooperate with a non-return resilient member and the second end (D) comprising a hollow, a surface of which is intended to form a stop surface for the non-return resilient member.

17. The assembly according to claim 16, wherein the substrate has a substantially parallelepipedal shape and in that, along a cutting plane interposed between the upstream and downstream faces and passing through the first (C) and second (D) ends, the substrate has a parallelogram shape, the ramp being situated at a first vertex arranged on the same side as the first end (C) of the substrate and the hollow being situated at a second vertex arranged on the same side as the second end (D) of the substrate.

18. The assembly according to claim 17, wherein the shape of the substrate is substantially rectangular and/or in that the first vertex and the second vertex are connected by the same edge extending between the first and second ends of the substrate.

19. The assembly according to claim 17, wherein the ramp is substantially planar and obliquely inclined.

20. The device according to claim 6, wherein the guide comprises a U-shaped rectilinear rail is covered by a rectilinear cover, having a U shape, carrying at one end a non-return resilient member allowing the introduction of the substrate in the first opening and preventing removal thereof from the movement path through the first opening, and at another end a restriction resilient member configured so as to restrict the discharge of the substrate through the second opening.

21. The device according to claim 7, wherein the guide comprises a U-shaped rectilinear rail is covered by a rectilinear cover, having a U shape, carrying at one end a non-return resilient member allowing the introduction of the substrate in the first opening and preventing removal thereof from the movement path through the first opening, and at another end the restriction resilient member configured so as to restrict the discharge of the substrate through the second opening.

22. The device according to claim 6, wherein the non-return resilient member and a restriction resilient member configured to restrict the discharge of a substrate through the second opening each comprise a resilient blade.

* * * * *